United States Patent [19]

Reyes

[11] Patent Number: 5,105,821

[45] Date of Patent: * Apr. 21, 1992

[54] INTERFACE CABLE FOR CONNECTING BEDSIDE ELECTROCARDIOGRAPH MONITOR TO PORTABLE DEFIBRILLATOR/ELECTROCARDIOGRAPH MACHINE

[76] Inventor: Rey S. Reyes, 26784 Via San Jose, Mission Viejo, Calif. 92691

[*] Notice: The portion of the term of this patent subsequent to Dec. 4, 2007 has been disclaimed.

[21] Appl. No.: 538,984

[22] Filed: Jun. 15, 1990

Related U.S. Application Data

[63] Continuation of Ser. No. 381;456, Jul. 18, 1989, Pat. No. 4,974,600.

[51] Int. Cl.$^5$ .............................................. A61N 1/08
[52] U.S. Cl. ................. 128/696; 128/419 D; 364/413.06
[58] Field of Search ............ 128/696, 710, 419 D, 128/419 R, 419 P; 364/413.06, 413.02

[56] References Cited

U.S. PATENT DOCUMENTS

| | | | |
|---|---|---|---|
| 2,029,844 | 2/1936 | Tyler | 99/18 |
| 2,220,285 | 11/1940 | Rodd | 248/313 |
| 2,419,040 | 4/1947 | Stepanian | 211/74 |
| 2,557,801 | 6/1951 | Shapiro | 211/75 |
| 3,538,484 | 11/1970 | Passafiume | 339/28 |
| 3,547,108 | 12/1970 | Seiffert | 128/2.06 |
| 3,865,101 | 2/1975 | Saper et al. | 128/2.06 R |
| 4,096,856 | 6/1978 | Smith et al. | 128/4.19 D |
| 4,106,494 | 8/1978 | McEachern | 128/2.06 B |
| 4,164,215 | 8/1979 | Finlayson et al. | 128/696 |
| 4,193,588 | 3/1980 | Doneaux | 269/47 |
| 4,419,998 | 12/1983 | Heath | 128/639 |
| 4,494,552 | 1/1985 | Heath | 128/696 |
| 4,498,594 | 2/1985 | Elder | 211/181 |
| 4,550,370 | 10/1985 | Baker | 364/413 |
| 4,589,556 | 5/1986 | Peretz | 211/41 |
| 4,628,935 | 12/1986 | Jones et al. | 128/419 D |
| 4,653,474 | 3/1987 | Reithler | 128/1 R |
| 4,840,186 | 6/1989 | Lekholm et al. | 128/784 |

FOREIGN PATENT DOCUMENTS

| | | |
|---|---|---|
| 3234441 | 5/1984 | Fed. Rep. of Germany . |
| 360952 | 5/1906 | France . |
| 1055752 | 2/1954 | France . |
| 1217601 | 5/1960 | France . |
| 2023271A | 12/1979 | United Kingdom . |

Primary Examiner—William E. Kamm
Assistant Examiner—Scott M. Getzow

[57] ABSTRACT

An interface cable for connecting a monitor output jack to a defibrillator/ECG machine patient input connector. The interface cable comprises a length of flexible cable having a first (monitor) and a second (defibrillator) end. A plug or connector mounted on the first (monitor) end of the interface cable is sized and configured to be insertable and/or otherwise connectable with the output jack or output connection of the bedside monitor. A plug or connector positioned on the second (defibrillator) end of the interface cable is sized and configured to be insertable into and/or otherwise connectable with the input jack/input connector of the defibrillator/ECG machine. Thus, the interface cable is usable to establish rapid electrical interconnection between the output jack of a bedside monitor and the patient input connector of a defibrillator/ECG machine.

2 Claims, 1 Drawing Sheet

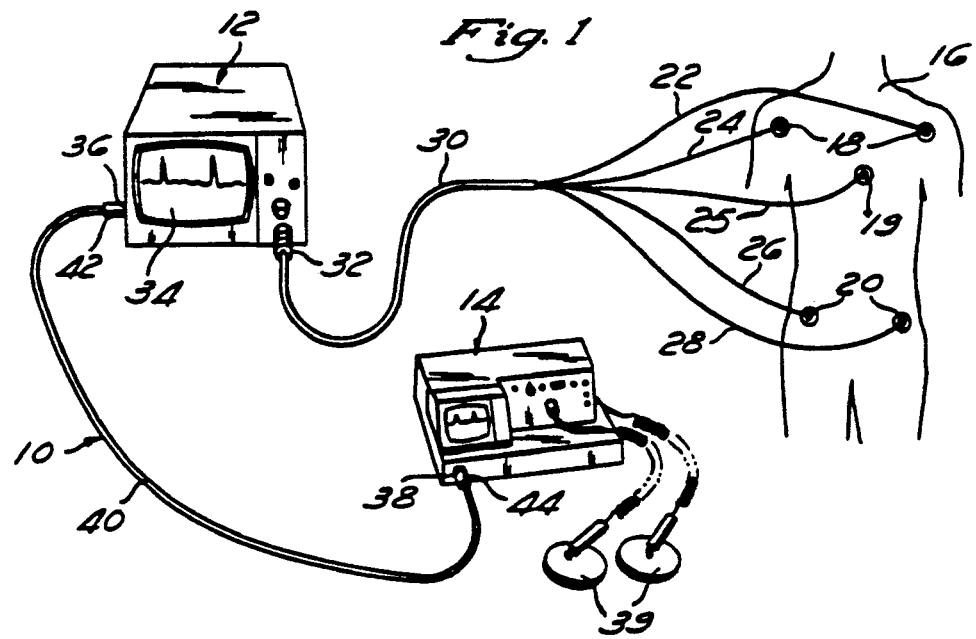
Fig. 1
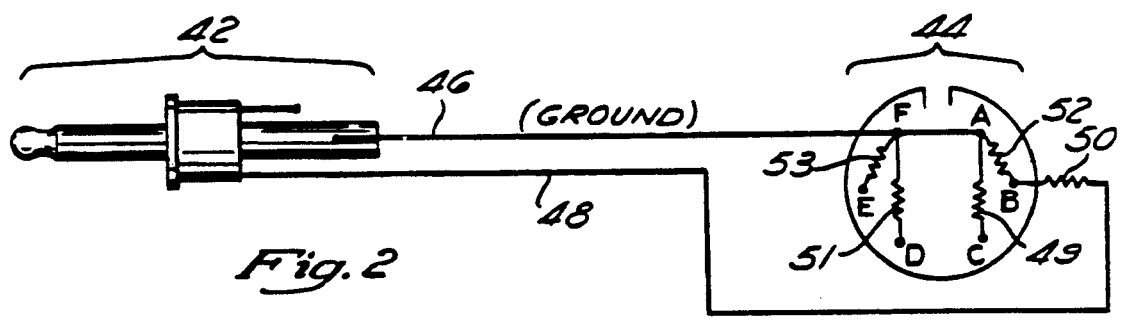
Fig. 2
Fig. 3a
Fig. 3b
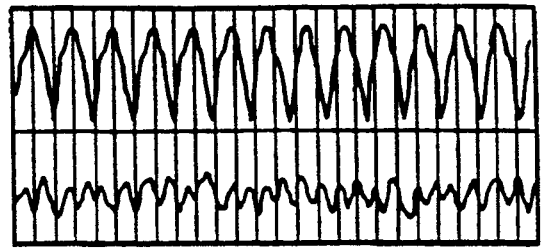

INTERFACE CABLE FOR CONNECTING BEDSIDE ELECTROCARDIOGRAPH MONITOR TO PORTABLE DEFIBRILLATOR/ELECTROCARDIOGRAPH MACHINE

This application is a continuation of application Ser. No. 07/381,456, filed Jul. 18, 1989, now U.S. Pat. No. 4,974,600.

FIELD OF THE INVENTION

The present invention relates generally to medical equipment, and more particularly to a device for establishing rapid electrical interconnection between a bedside electrocardiograph monitor and a portable defibrillator/electrocardiograph machine used to administer emergency life support treatment.

BACKGROUND OF THE INVENTION

In most hospital critical care settings, bedside patient monitors are routinely employed for real time monitoring and display of the patient's electrocardiogram (ECG) and/or other clinically important variables.

The types of bedside monitors employed range from simple, relatively portable, single channel ECG monitors to larger, more complex multi-channel monitors. Typically, the simple, one channel ECG monitors incorporate a small screen for displaying the patient's ECG. The typical multi-channel bedside monitor consist of a larger, wall mounted unit having one or more display screens whereupon multiple variables, tracings or physiological waveforms (ECG, arterial pressure, central venous pressure, pulmonary artery pressure, respiratory flow, etc.) may be simultaneously displayed.

Most, if not all commercially available bedside monitors incorporate signal output jacks for each channel displayed. Ancillary devices such as strip chart recorders may then be connected to these signal output jacks by way of connecting cables, wires, or other interconnection means.

In normal operation, the bedside ECG monitor receives input (i.e. sensed voltage changes from various points on the patient's body) from a plurality of skin-contacting electrodes positioned at selected anatomical points on the patient's body. Adhesive patch type electrodes are most frequently employed because they are comfortable for the patient to wear and tend to remain in their desired positions without need for attachment of retainer bands, straps, or other attachment means. Pectoral lead electrodes are placed in contact with the arms, or shoulders of the patient, while pelvic lead electrodes are placed in contact with the legs or lower quadrants of the patient's abdomen. Also, if it is desired to effect monitoring of ECG leads V1 through V6, an additional chest electrode must be provided for attachment to prescribed points on the patient's chest. Thus, as many as five separate electrodes may remain attached to the patient during routine bedside ECG monitoring.

A "patient cable" is employed to carry the sensed ECG voltage changes from the skin contacting ECG electrodes to the bedside ECG monitor. Typically, such "patient cable" comprises a length of electrically conductive cable. The proximal end of the cable is provided with a plug or connector for attachment to the bedside monitor. The distal end of the cable is furcated into as many as five (5) separate wires or cables, each such furcated segment being independently connectable to skin-contacting ECG electrodes (e.g. two (2) pectoral electrodes, two (2) pelvic electrodes, and/or one (1) chest electrode).

The primary purpose for bedside ECG monitoring in critical care facilities is to effectuate rapid detection and treatment of cardiac arrhythmias and/or cardiac arrest. Upon detection of a serious or life threatening cardiac arrhythmia, it is desirable to administer anti-arrhythmic treatment as rapidly as possible. Some cardiac arrhythmias are preferrably treated by administration of anti-arrhythmic drugs while other cardiac arrhythmias are preferrably treated by immediate electroshock (i.e. DC cardioversion).

In treating arrhythmias for which emergency cardioversion is the treatment of choice, it is common practice to deploy a portable defibrillator/ECG machine to the bedside. Such portable defibrillator/ECG machine incorporates a small ECG monitor in combination with an electroshock machine having paddle type electrodes. The paddle type electrodes are positionable in contact with the patient's chest so as to administer a timed electroshock to the arrhythmic heart. The defibrillator/ECG machine incorporates internal synchronizing circuitry whereby the delivery of the electroshock is timed in accordance with the patient's ECG activity. Such timed delivery of the electroshock is particularly important in certain arrhythmias (e.g. ventricular tachycardia) wherein it is desirable to administer the electroshock at a specific point during the cardiac contraction cycle. An ill timed electroshock of the heart during ventricular tachycardia may cause the heart to regress to a state of fibrillation while a properly timed electroshock is likely to effect successful cardioversion of the ventricular tachycardia to a relatively normal sinus rhythm.

Although DC cardioversion offers an effective means for treating certain life threatening cardiac arrhythmias, it must be appreciated that the speed with which such treatment is delivered may be of great importance. For example, critically ill patients who experience unstable ventricular tachycardia are likely to further degenerate into ventricular fibrillation within a short time (e.g. 2–5 minutes) if DC cardioversion is not undertaken. Once the heart has lapsed into fibrillation, the chances for successful recussitation of the patient are substantially lessened. Thus it is highly desirable to electroshock the heart as rapidly as possible when ventricular tachycardia is detected.

The time required to deliver the electroshock is largely devoted to deployment, set up and preparation of the defibrillator/ECG machine. In setting up the defibrillator/ECG machine it is generally necessary to attach a second patient cable and/or a second set of skin contacting electrodes to effect input of the ECG signal to the defibrillator/ECG machine.

To wit: upon detection of a cardiac arrhythmia treatable by DC cardioversion, it is generally necessary for the critical care staff personnel to rapidly apply at least three and sometimes as many as five additional ECG electrodes to the patient's body and to subsequently deploy a secondary patient cable to interconnect the newly applied ECG electrodes to the defibrillator/ECG machine. The attachment of additional electrodes, and the deployment of a second "patient cable" is time consuming and generally redundant in view of the fact that patient's who are connected to a bedside ECG monitor are already outfitted with a full set of properly positioned ECG electrodes and connected to the bedside monitor by way of a standard patient cable. While it would seem a simple matter to merely extract the proximal end of the patient cable from the bedside monitor and, alternately, insert it into the input jack of the defibrillator/ECG machine, such is oftentimes non-feasible because the size and/or configuration of the patient/cable connector is incompatable with the input jack of the defibrillator/ECG machine.

In light of the compelling need for rapid deployment and effectuation of emergency cardioversion, there exists a need in the art for a means for rapidly connecting a portable defibrillator/ECG machine to the output jack of a functional bedside ECG monitor so as to eliminate the need for attachment of additional ECG electrodes and/or deployment of a second "patient cable".

BRIEF SUMMARY OF THE INVENTION

The present invention overcomes some or all of the shortcomings of the prior art by providing a method and device for rapidly connecting a bedside ECG monitor to a portable defibrillator/ECG machine such that the ECG signal displayed on the ECG monitor will be fed, from the monitor, to the separate defibrillator/ECG machine.

In accordance with the invention, there is provided an interface cable for connecting a monitor output jack to the patient input connector of a defibrillator/ECG machine. Preferably, the interface cable of the present invention comprises a length of flexible cable having a first (monitor) and a second (defibrillator) end. A plug or connector mounted on the first (monitor) end of the interface cable is sized and configured to be insertable and/or otherwise connectable with the output jack or output connection of the bedside monitor. A plug or connector positioned on the second (defibrillator) end of the interface cable is sized and configured to be insertable into and/or otherwise connectable with the input jack/input connector of the defibrillator/ECG machine. Thus, the interface cable is usable to establish rapid electrical interconnection between the output jack of a bedside monitor and the input jack of a defibrillator/ECG machine.

In a preferred embodiment, the plug or connector mounted on the first "monitor" end of the interface cable comprises a single prong phone or stereo plug insertable into a standard single prong output jack of a standard bedside ECG monitor.

Also, in a preferred embodiment of the invention, the plug or connector mounted on the second (defibrillator) end of the interface cable comprises a specialized plug or connector (e.g. a six pin male connector) compatable with the patient input connector and manufacturers specifications of a particular portable defibrillator/ECG machine.

The interface cable of the present invention functions to carry the ECG signal from the bedside monitor to the attendant defibrillator/ECG machine without substantial delay or alteration of the signal. Avoiding substantial delay or alteration of the signal is critical in that, if the defibrillator/ECG machine were to receive a signal which is out of phase or otherwise distorted, such could result in ill timed delivery of the electroshock pulse from the defibrillator unit.

A principal object of the invention is to provide a method and device for effecting rapid interconnection between a bedside ECG monitor and a portable defibrillator/ECG unit.

A further object of the invention is to minimize the elapsed time between the initial detection of a life threatening cardiac arrhythmia and the therapeutic delivery of DC electroshock by a portable defibrillator/ECG machine.

Further objects and advantages will become apparent to those skilled in the art upon reading and understanding of the following detailed description and the accompanying drawings.

BRIEF DESCRIPTION OF THE DRAWINGS

FIG. 1 is a schematic showing of a critical care patient connected to a bedside ECG monitor and wherein an interface cable of the present invention connects the output jack of the bedside ECG monitor to the input jack of a portable defibrillator/ECG unit.

FIG. 2 is a schematic wiring diagram of a preferred interface cable of the present invention.

FIG. 3A shows a lead II electrocardiogram depicting normal sinus rhythm.

FIG. 3B shows a lead II electrocardiogram illustrating ventricular tachycardia (upper strip) and ventricular fibrillation (lower strip).

DETAILED DESCRIPTION OF A PREFERRED EMBODIMENT

The following description is provided for purposes of describing and illustrating a presently preferred embodiment of the invention and is not intended to limit the scope of the invention in any way.

As shown in the schematic diagram of FIG. 1, the interface cable 10 of the present invention serves to electrically interconnect a patient bedside monitor 12 to an ECG unit 14.

As shown, the patient 16 is lying in a dorsally recumbant position with two (2) pectoral lead electrodes 18, one (1) chest lead electrode and two (2) pelvic lead electrodes 20 positioned on the anterior portions of the patient's thorax and lower abdomen, respectively. The pectoral electrodes 18 are connected to pectoral limb furcations or leads 22, 24 of patient cable 30. Chest electrode 19 is connected to the left side of the thorax while pelvic electrodes 20 are connected to pelvic limb furcations or leads 26, 28. The patient cable 30 is provided with an input connector 32 mounted on the proximal end thereof. Such input connector is insertable into the ECG channel input jack of the bedside monitor 12. Thus, the patient's electrocardiogram is continually monitored by and displayed on the screen 34 of bedside monitor 12.

In the event that the patient 16 requires DC cardioversion and/or defibrillation, it is desirable to connect the defibrillator/ECG unit 14 directly to the ECG electrodes 18, 20 already mounted on the patient, or to provide additional electrodes and a separate patient cable for connection of the defibrillator/ECG unit 14 to the patient 16. However, in the devices of the prior art, the patient cable plug 32 is not sized or configured to be connectable to the defibrillator/ECG unit 14. Moreover, even if the patient cable 30 were connectable to the defibrillator/ECG unit 14, its disconnection from the monitor 12 would preclude further viewing of the electrocardiogram on the monitor screen 34. Alternately, the provision and connection of a separate patient cable and electrodes requires at least one (1) minute and sometimes as much as three (3) minutes. The utilization of as much as three (3) minutes to merely attach the defibrillator/ECG unit 14 to the patient is unacceptable in view of the potential lethality of certain arrhythmias (e.g. ventricular tachycardia) if allowed to continue uncorrected.

Accordingly, the interface cable 10 of the present invention provides a means whereby the electrocardiograph signal may be transmitted directly from the output jack 36 of the bedside monitor 12 to the patient input connector 38 of the defibrillator/ECG machine 14. The interface cable 10 of the preferred embodiment shown comprises approximately 15 feet of shielded 2 conductor, 22 gauge cable whereby a 1 volt ECG signal may be transported from the bedside monitor 12 to the defibrillator/ECG unit 14. A monitor plug 42 positioned on the first (monitor) end of the interface cable 10 is sized and configured to fit into the output jack 36 of monitor 12. In most prior art monitoring devices, a standard stereo phono plug connector may be employed for this purpose. As shown in the schematic of FIG. 2, the standard stereo plug connector 42 comprises a single male prong extending from the body of the connector. First 46 and second 48 cable conductors or wires are connected to the internal contact points of the connector 42.

On the second (defibrillator) end of the cable 40, there is provided a defibrillator/ECG connector 44 which is sized and configured to be insertable into the input jack 38 of defibrillator/ECG machine 14.

In most commercially available defibrillator/ECG machines (e.g. the "Lifepack 6" Cardiac Care System, Physio-Control, Inc. 11811 Willows Road, Redmond, Wash. 98052), an input amplifier and/or signal conditioner is positioned internal of the the device and is adapted to receive input from a patient lead cable having five separate patient-contacting electrodes disposed thereon. Thus, such devices are typically adapted to receive a six pin type connector within the ECG input jack 38. Accordingly although the interface cable 10 of the present invention carries only a single ECG signal from the output jack of the monitor 12, it is nonetheless necessary for the defibrillator/ECG connector 44 of this preferred interface cable 10 to be insertable or otherwise physically compatible with the female six prong input jack 38 of the defibrillator/ECG unit 14.

As shown in the schematic electrical diagram of FIG. 2, the monitor plug 42 which inserts into the output jack 36 of bedside monitor 12 comprises a standard, single prong, male phono plug or the like. Line 46 is connected to the ground post of connector 42 while the second line 48 is connected to the positive (+) post of connector 42.

At the other end of the cable 40, line 46 is connected to pins F and A of six pin defibrillator/ECG connector 44 while line 48 is connected to a first resistor 50 which is in turn connected to pin B of such connector 44. A second resistor 52 connects pin B to pin A.

The first resistor 50 is of greater electrical resistance than the second resistor 52. In this preferred embodiment, the first resistor 50 comprises a carbon type 100 k ohm, ¼ watt at ±5% resistor. The second resistor 52 comprises a carbon type 100 ohm at ±5% resistor.

Additional resistors, 49, 51 and 53 are provided to disable unused pins C, D and E of connector 44. In this preferred embodiment, resistors 49, 51 and 53 comprise 100 ohm ±5% resistors.

The attachment of lines 46 and 48 to connector 44 and the arrangement of first and second resistors 50 and 52 thereon serves to render the defibrillator/ECG connector 44 of this preferred embodiment functional as a signal impedance matching network, connectable to the patient input connector and compatible with the input amplifier of a preferred defibrillator/ECG unit 14. It will be appreciated, however, that other resistor arrangements and connections in series/parallel will permit use of the interface cable 10 of the present invention in conjunction with other input amplifiers and other types of defibrillator/ECG units. As an example, resistors 49-53 form a network of resistors for loading the input amplifiers of the defibrillator/ECG machine 14, and for isolating the monitor 12 from the defibrillator/ECG machine 14, when the machine connector 44 is connected to the input jack 38. In the preferred embodiment the network of resistors includes a plurality of low impedance resistors 49, 51-53, each resistor establishing a low resistive path between the ground wire 46 and one of the input amplifiers of the defibrillator/ECG machine, whereby the input signal comparison and alarm circuit of the defibrillator/ECG machine 14 is prevented from triggering since the low impedance resistors simulate the normal inputs of the several patient leads 22, 24, 25, and 28. The high impedance resistor 50, establishes a high resistive path between the signal wire 48 and one of the input signal amplifiers, whereby the signal output circuit of the monitor and the input circuit of the defibrillator/ECG machine are maintained in relative isolation in order to match these circuits without undue loading of one circuit on the other which could cause signal degradation.

OPERATION OF THE PREFERRED EMBODIMENT

An exemplary situation in which the preferred interface cable 10 of the present invention is usable is that in which a critical care patient 16 who is being monitored by a bedside electrocardiograph monitor 12 exhibits a period of unstable, sustained ventricular tachycardia.

To enhance the reader's understanding of such exemplary situation, the accompanying drawings include several illustrations of electrocardiographic tracings.

When the occurrence of unstable ventricular tachycardia is identified, current clinical practice calls for the delivery of direct current countershock (20–50 joules) to the myocardium while the heart remains in ventricular tachycardia. Of course, in view of the propensity for degeneration to ventricular fibrillation, it is desirable that the countershock be administered as rapidly as possible. Furthermore, because ventricular tachycardia comprises rhythmic, albeit abnormal, electrical activity of the heart, it is necessary that such DC countershock be delivered at a precise point in the cardiac cycle. Delivery of the electroshock at the wrong point of the cardiac cycle could work a deleterious result (e.g. precipitation of fibrillation) rather than bringing about the desired result of cardioversion to normal sinus rhythm. Accordingly, to effect the clinically indicated DC countershock, it is necessary that the patient be rapidly conntected to a separate defibrillator/ECG machine having internal circuitry whereby the DC countershock may be delivered at the desired point on the cardiac contractile cycle.

In using the emergency cardioversion equipment of the prior art, it has heretofore been necessary to deploy a separately dedicated patient cable, and/or to attach a separate set of ECG electrodes, to the patient in order to establish the necessary input links between the patient and the defibrillator ECG machine. The deployment of such specially dedicated patient cable and additional electrodes has proven to be time consuming and may substantially delay the delivery of therapeutic electroshock from the defibrillator.

The interface cable 10 of the present invention eliminates the need for deployment of a separately dedicated patient cable and/or additional ECG electrode, thereby minimizing the elapsed time between the initial detection of the cardiac arrhythmia and the delivery of the therapeutic electroshock.

In accordance with the present invention, upon initial recognition of the cardiac arrhythmia (either by direct observation or by emission of an auditory alarm from the bedside monitor 12), the portable defibrillator/ECG machine will be immediately brought to the patient's bedside as shown in FIG. 1. Thereafter, without disturbing the existing placement of patient cable 30 and electrodes 18, 20, the portable defibrillator/ECG machine 14 will be connected to the output jack of the bedside monitor 12 by way of the interface cable 10 of the present invention. The defibrillator/ECG connector 44 positioned on the second (defibrillator) end of the cable 40 is inserted into patient input connector 38 of defibrillator/ECG machine 14. The bedside monitor plug 42 positioned on the first (monitor) end of the cable 40 is inserted into the ECG channel output jack 36 of the bedside monitor 12. Thus, the ECG signal of the ECG lead being displayed on the bedside monitor 12 is transferred from output jack 36 of the monitor 12 to patient input connector 38 of the defibrillator/ECG machine 14. Provided that the interface cable 10 does not substantially delay or distort the ECG signal, the defibrillator/ECG machine 14 will receive a real time ECG tracing sufficient to enable its use for the purpose of emergency cardioversion. Accordingly, the paddle electrodes 39 may be placed in contact with the patient's chest, and the defibrillator/ECG machine 14 may be thereby employed to deliver the therapeutic DC countershock as required.

By the above stated method of operation, the interface cable 10 of the present invention permits rapid delivery of DC countershock without the need for removing and/or replacing the patient cable 30 and/or electrodes 18, 20. The elimination of such unnecessary steps saves critical time in the delivery of this all-important therapeutic measure.

Although the invention has been described herein with reference to presently preferred embodiments thereof, it will be appreciated that various alterations, additions and deletions may be made to such embodiments without departing from the spirit and scope of the invention.

What is claimed is:

1. An apparatus for defibrillation comprising:
 a bedside electrocardiograph monitor having an ECG signal output jack, the output jack having at least one amplified ECG signal;
 a defibrillator/ECG machine having a plurality of input signal amplifiers, an input signal comparison and alarm circuit, and an ECG input jack, the input jack being interconnected with each of the signal amplifiers;
 an interface cable having a segment of electrically conductive cable having a first end and a second end, the cable containing a ground wire and a signal wire, a monitor connector positioned on the first end of said cable, said monitor connector being sized and configured for direct connection to said ECG output jack of said bedside electrocardiograph monitor, the at least one amplified ECG signal being connected to the signal wire when the monitor connector is connected to the output jack, and a defibrillator/ECG machine connector positioned on the second end of said cable, said defibrillator/ECG machine connector being sized and configured for direct connection to the ECG input jack of said defibillator/ECG machine, the machine connector having a network of resistors for loading the input amplifiers, and to isolate the monitor from the defibrillator/ECG machine, when the machine connector is connected to the input jack.

2. The apparatus of claim 1 wherein the network of resistors includes a plurality of low impedance resistors, each resistor establishing a low resistive path between the ground wire and one of said input amplifiers, whereby the input signal comparison and alarm circuit is prevented from triggering and wherein the load network includes a high impedance resistor, the high impedance resistor establishing a high resistive path between the signal wire and one of said input signal amplifiers, whereby the signal output circuit of the monitor and the input circuit of the defibrillator/ECG machine are maintained in relative isolation.

* * * * *